United States Patent [19]
Helmus et al.

[11] Patent Number: 5,569,463
[45] Date of Patent: Oct. 29, 1996

[54] MEDICAL DEVICE POLYMER

[75] Inventors: Michael N. Helmus, Worcester; M. Joshua Tolkoff, Brookline; Carol L. Raleigh, Weston, all of Mass.

[73] Assignee: Harbor Medical Devices, Inc., Jaffrey, N.H.

[21] Appl. No.: 479,513

[22] Filed: Jun. 7, 1995

Related U.S. Application Data

[62] Division of Ser. No. 152,876, Nov. 15, 1993, Pat. No. 5,447,724, which is a continuation of Ser. No. 525,339, May 17, 1990, abandoned.

[51] Int. Cl.$^6$ .............................. A61F 2/04; A01N 1/02; A61M 5/32
[52] U.S. Cl. .......................... 424/426; 424/423; 424/424; 424/425; 424/450; 427/2.12; 514/772.2; 514/822; 523/112; 523/113; 604/53; 604/266; 623/12
[58] Field of Search .................................... 424/426, 423, 424/424, 425, 450; 427/2.12; 514/772.2, 822; 523/112, 113; 604/53, 266; 623/12

[56] References Cited

U.S. PATENT DOCUMENTS

| | | | |
|---|---|---|---|
| 3,663,288 | 5/1972 | Miller | 424/423 |
| 3,705,938 | 12/1972 | Hyman et al. | 424/423 |
| 3,715,277 | 2/1973 | Dinelli et al. | 435/182 |
| 3,864,468 | 2/1975 | Hyman et al. | 424/423 |
| 3,932,656 | 1/1976 | Ramwell et al. | 424/423 |
| 4,054,139 | 10/1977 | Crossley | 604/265 |
| 4,116,898 | 9/1978 | Dudley et al. | 424/78.27 |
| 4,164,560 | 8/1979 | Folkman et al. | 424/486 |
| 4,326,532 | 4/1982 | Hammar | 604/266 |
| 4,343,788 | 8/1982 | Mustacich et al. | 514/578 |
| 4,353,996 | 10/1982 | Marconi et al. | 523/105 |
| 4,357,312 | 11/1982 | Hsieh et al. | 424/425 |
| 4,391,797 | 7/1983 | Folkman et al. | 424/425 |
| 4,400,374 | 8/1983 | Cardarelli | 424/486 |

(List continued on next page.)

FOREIGN PATENT DOCUMENTS

| | | |
|---|---|---|
| 87311347 | 7/1988 | European Pat. Off. |
| WO89/02575 | 3/1989 | WIPO |

OTHER PUBLICATIONS

Literature Review of the Use of Heparinized Polyurethane Catheters: Comparison to Silicone and Non–Heparinized Catheters, Harbor Medical Devices, Jul., 1989, 1–2.

Polysciences, Inc., "TDMAC/Heparin Complex Coatings for Preparing Nonthrombogenic Plastic Surfaces", copyright Jul. 1980 Data Sheet No. 172.

Allen et al., "Reduction of Platelet Deposition on Vascular Graphs Using an Antiplatelet Graft Coating Technique", Abstract in Journal of Surgical Research, 16, 367/373 (1982).

Brown et al., "Controlled Release of Insulin From Polymer Matrices", Diabetes 35:684–691, 1986.

Ebert et al., "Heparin/Polymers for the Prevention of Surface Thrombosis", Medical Applications of Controlled Release, II:77–106.

Edelman et al., "Polymer Matrix Based Controlled Adventitial Delivery of Anti–Proliferative Agents and Regulation of the Vascular Response to Injury", p. 248.

(List continued on next page.)

Primary Examiner—Carlos Azpuru
Attorney, Agent, or Firm—Fish & Richardson P.C.

[57] ABSTRACT

A medical device and a method for its manufacture. The function of the medical device requires exposure of the device to the tissue of a patient. The device has a tissue-exposed portion constructed to release an agent that inhibits adverse reaction to the presence of the device defined by a polymeric surface-layer overlying in a supported manner a polymer defining a reservoir. The reservoir incorporates the agent in a manner that permits substantially free outward release of the agent from the reservoir and the overlying layer defines metering outward passages constructed to control the outward migration of the agent to enable prolonged release of the agent from the surface of the medical device to prevent the adverse reaction due to the presence of the device.

13 Claims, 6 Drawing Sheets

U.S. PATENT DOCUMENTS

| | | | |
|---|---|---|---|
| 4,479,795 | 10/1984 | Mustacich et al. | 604/53 |
| 4,481,323 | 11/1984 | Sterling | 524/269 |
| 4,515,593 | 5/1985 | Norton | 604/265 |
| 4,557,724 | 12/1985 | Gregonis et al. | 604/49 |
| 4,581,028 | 4/1986 | Fox, Jr. et al. | 623/2 |
| 4,592,920 | 6/1986 | Murtfeldt | 427/2 |
| 4,603,152 | 6/1986 | Laurin et al. | 604/265 |
| 4,627,850 | 12/1986 | Deters et al. | 604/892.1 |
| 4,663,308 | 5/1987 | Saffran et al. | 514/3 |
| 4,670,313 | 6/1987 | Saudagar | 428/12 |
| 4,676,975 | 6/1987 | McGary et al. | 424/423 |
| 4,789,720 | 12/1988 | Teffenhart | 528/76 |
| 4,810,543 | 3/1989 | Gould et al. | 219/10.43 |
| 4,844,986 | 7/1989 | Karakelle et al. | 428/447 |
| 4,861,627 | 8/1989 | Mathiowitz et al. | 427/213.31 |
| 4,874,373 | 10/1989 | Luther et al. | 604/164 |
| 4,891,225 | 1/1990 | Langer et al. | 424/408 |
| 4,898,734 | 2/1990 | Mathiowitz et al. | 424/426 |
| 4,900,556 | 2/1990 | Wheatley et al. | 424/450 |
| 4,906,465 | 3/1990 | Chaikof et al. | 623/1 |
| 4,906,474 | 3/1990 | Langer et al. | 514/772 |
| 4,925,668 | 5/1990 | Khan et al. | 424/422 |
| 4,946,929 | 8/1990 | D'Amore et al. | 528/206 |
| 4,999,210 | 3/1991 | Soloman et al. | 427/2 |
| 5,447,724 | 9/1995 | Helmus et al. | 424/426 |

OTHER PUBLICATIONS

Kim et al., "Heparin Release From Hydrophobic Polymers: (1) In Vitro Studies", Archives of Pharmacal Research 9:193–199, 1986.

Kim, "Heparinized Polymers for Improving Blood Compatibility", MD&DI 99–103, 1984.

Lin et al., "Minimum Heparin Release Rate for Nonthrombogenicity", Trans. Am Soc. Artif. Intern. Organs XXXIII:602–605, 1987.

McRea et al., "Prostagladin Releasing Polymers–Stability and Efficacy", Trans. Am Soc. Artif. Intern. Organs XXVII:511–516, 1981.

Miyama et al., "A New Antithrombogenic Heparinized Polymer", J. Biomed Mater. Res. 11:251–265, 1977.

Noishiki et al., "Prevention of Thrombosis–Related Complications in Cardiac Catheterization and Angiography Using a Heparinized Catheter (Anthron®)", ASAIO Jul.–Sep. 10:359–365, 1987.

Rhine et al., "Polymers for Sustained Macromolecule Release: Procedures to Fabricate Reproducible Delivery Systems and Control Release Kinetics", J. of Pharmaceutical Sciences 69:265–270, 1980.

Ritschel et al., "Permeability of [$^3$H] Water Across a Porous Polymer Matrix Used as Rate–Limiting Shell in Compression–Coated Tablets", J. of Controlled Release 97–101, 1990.

Wilson et al., "Heparinized Polymers as Thromboresistant Biomaterials", Polym.–Plast. Technol. Eng., 16:119–208, 1981.

Sparks, "Reduction of Platelet Deposition on Vascular Graphs using an Anti–platelet Graft Coating Technique" Abstract, J. of Surgical Research 33:367–373, 1982.

Technical Note: "Literature Review of the Use of Heparinized Polyurethane Catheters: Comparison to Silicone and Non–Heparinized Catheters."

MEDICAL DEVICE POLYMER

This is a divisional of application Ser. No. 08/152,876, filed Nov. 15, 1993, now U.S. Pat. No. 5,447,724 which was a continuation of U.S. Ser. No. 07/525,339, filed May 17, 1990 and now abandoned.

FIELD OF THE INVENTION

This invention relates to medical devices that release physiologically active agents to prevent adverse reactions to the device, and their manufacture and use.

BACKGROUND OF THE INVENTION

Exposure of a foreign material to body fluids sometimes produces adverse physiological reactions. This is true in particular for medical devices, e.g., of metal or plastic, that require contact with blood. Adverse reactions include the formation of thrombus, i.e., clotting on the exposed surfaces of the device which can cause blockage of tubular devices such as catheters or cause emboli to form which can enter the blood stream and block smaller blood vessels, leading to organ damage or stroke. To reduce the complications arising from thrombus formation an anticoagulant such as heparin is sometimes administered to prevent clot formation in or on the device. Heparin coatings have also been applied to polymer medical device substrates.

In addition no inhibiting clot formation, it is useful to inhibit other adverse reactions to medical devices such as cell proliferation which can lead to hyperplasia, occulsion of blood vessels, platelet aggregation, rejection of artificial organs, infection, calcification and to enhance tissue growth function.

SUMMARY OF THE INVENTION

In one aspect, the invention features a medical device the function of which requires exposure to the tissue of a patient. The medical device has a tissue-exposed portion constructed to release an agent that inhibits adverse reaction to the presence of the device. The portion is defined by a polymer surface-layer overlying in a supported manner a polymer defining a reservoir. The reservoir incorporates the agent in a manner that permits substantially free outward release of the agent from the reservoir and the overlying layer defines metering outward passages constructed to control the outward migration of the agent to enable prolonged release of the agent from the surface of the medical device to prevent the adverse reaction due to the presence of the device.

Various embodiments of the device may include the following features. The surface-layer incorporates an elutable component to enable formation of pore structure in the surface-layer by solubilizing of the elutable component by the tissue during exposure. The tissue-exposed portion is a coating covering the surface of the medical device or the device is formed substantially from the tissue-exposed portion. The reservoir and surface-layer are each less than about 100 mils thick, preferably about 2 to 3 mils thick.

Embodiments of the device may further include the following. The tissue-exposed portion is constructed for prolonged release of the agent for a period corresponding to the duration of the exposure of the device to blood. The tissue-exposed portion is constructed for release at effective levels for at least about 200 hours. The reservoir is comprised of more than about 30% by weight of the agent, preferably about 40 to 60% by weight of the agent. The reservoir includes a non-physiologically active elutable component The agent is selected from an antithrombogenic drug such as heparin, antiplatelet drug such as aspirin, a prostaglandin such as prostacyclin, a thrombolytic drug, such as tPA, urokinase, streptokinase, prourokinase or an antiproliferative drug such as heparin or asteroid such as cortisone, an antirejection drug such as cyclosporin, an antimicrobial drug such as Vancomycin, a growth factor such as epidermal growth factor, platelet growth factor and fibroblast growth factor and an anticalcifying agent such as a diphosphonate. The agent is in particulate form with a particle size about the thickness of the reservoir or less or preferably less than about 10 micron particle size.

Embodiments of the device may also include the following. The surface-layer is less than about 20% by weight of the elutable component preferably about 10 to 20% by weight of the elutable component. The elutable component is in colloidal regions and selected from polyethylene oxide, polyethylene glycol, polyethylene oxide/polypropylene oxide copolymers, polyhydroxyethylmethacrylate, polyvinylpyrollidone, and polyacrylamide and its copolymers and liposomes. The polyethylene oxide has a molecular weight of less than about 100,000. The elutable component is in particulate form and selected from albumin, dextran, proteins, peptides, polysaccharides, biodegradeable polymers and soluble cellulosics such as hydroxypropyl cellulose. The elutable component is a biodegradeable polymer selected from the group consisting of polylactides, polygalactides, polyanhydrides, polyorthoesters and their copolymers. The elutable component is a physiologically active agent. The surface-layer incorporates a minor amount of the physiologically active agent prior to exposure to blood. The elutable component creates regions of about 50 microns or less in he surface-layer, preferably, about 10 microns or less or submicron in size.

Embodiments of the device may also include the following. The surface layer and reservoir polymer are a polymer selected from polyurethane and its copolymers, silicone and its copolymers, ethylene vinylacetate, thermoplastic elastomers, polyvinylchloride, polyolefins, cellulosics, polyamides, polytetrafluoroethylenes, polyesters, polycarbonates, polysulfones, acrylics such as polymethylmethacrylate, and acrylonitrile butadiene styrene copolymers. The tissue exposed-portion has a durometer approximately equal to or less than the durometer of the medical instrument substrate. The reservoir and the outer layer are formed from the same polymer.

Embodiments of the device may further include The following. The coating covers a surface formed from a material selected from polyurethane and its copolymers, silicone and its copolymers, ethylene vinyl-acetate, thermoplastic elastomers, polyvinyl chloride, polyolefins, cellulosics, polyamides, polytetrafluoroethylenes, polyesters, polycarbonates, polysulfones, and acrylonitrile butadiene styrene copolymers; acrylics; metals, and alloys based on titanium, stainless steel, nickel-chrome, Nitinol or cobalt-chrome: ceramics of alumina and glass-ceramics such as Macor®. The medical device is selected from catheters, implantable vascular access ports, blood storage bags, vascular stents, blood tubing, central venous catheters, arterial catheters, vascular grafts, intraaortic balloon pumps, heart valves, cardiovascular sutures, total artificial heart and ventricular assist pump, extracorporeal devices such as blood oxygenators, blood filters, hemodialysis units, hemoperfusion units, plasmapheresis units, hybrid artificial organs such as pancreas or liver and artificial lungs.

In another aspect, the invention features a medical catheter device for use in blood-containing body lumens formed of a flexible catheter-defining substrate with a blood-exposed coating capable of substantially maintaining the flexibility of the catheter and constructed to release an anticoagulant agent that inhibits the formation of thrombus. The coating is defined by a polymeric surface-layer overlying in a supported manner a polymer defining a reservoir layer. The reservoir layer incorporates the anticoagulant agent to permit substantially free outward release of the agent from the reservoir. The overlying layer incorporates an elutable component, soluble in blood to enable formation of pore structure in the surface-layer by solubilizing of the elutable component by the blood during exposure. The pore structure defines metering outward passages constructed to control the outward migration of the agent to enable prolonged release of the agent from the surface of the medical device to prevent adverse reaction due To the presence of the device.

The medical catheter device may include the features of the medical device above. In addition, in particular, embodiments of the catheter may also include the following. The catheter substrate is a drug delivery catheter between about 2 to 12 French and the coating is about 6 mils thickness or less. The catheter is selected from implantable vascular access port catheters, central venous catheters, drug delivery catheters and angioplasty catheters.

In yet another aspect, the invention features a method for forming a medical device the function of which requires exposure to the blood of a patient, by providing a tissue-exposed portion to the device constructed to release an agent that inhibits adverse reaction to the presence of the device. The tissue exposed portion is provided by forming a polymeric reservoir portion incorporating the agent in a manner that permits substantially free outward release of the agent from the reservoir and forming an overlying surface-layer supported by the reservoir that defines metering outward passages constructed to control the outward migration of the agent to enable prolonged release of the agent from the surface of the medical device.

Embodiments of the method may also feature the following steps. The surface-layer is formed by incorporating into The surface-layer an elutable component to enable formation of pore structure defining the passages in the surface-layer by solubilizing of the elutable component by the tissue during exposure. The tissue-exposed portion is provided by forming a mixture including a reservoir polymer and the elutable component, forming the reservoir from the mixture, forming a mixture including a surface-layer polymer and the agent and applying the surface-layer mixture to the reservoir layer to form the surface-layer. The surface layer mixture is formed by mixing the surface-layer polymer and the elutable component in a solvent and evaporating the solvent to form the reservoir. The mixing involves mixing to suspend particulates or mixing to form a colloidal suspension in the solvent. For colloidal suspensions, the mixing may feature selecting the elutable component from polyethylene oxide, polyethylene glycol, polyethylene oxide/polypropylene oxide copolymers, polyhydroxyethyl methacrylate, polyvinylpyrollidone, and polyacrylamide and its copolymers and soluble cellulosics such as hydroxypropyl cellulose, polysaccharides and liposomes. The size and concentration of the elutable component is selected to produce a continuous network in the polymer.

Embodiments of the method may also include the following. The reservoir polymer and the agent are mixed in a solvent and the solvent evaporated to form the reservoir. The size and concentration of the agent are selected to produce a continuous network in the reservoir polymer.

Embodiments of the method may also include the following. The tissue exposed portion is applied as a coating to the surface of a medical device substrate. The tissue exposed portion is formed to be at least as flexible as the substrate. The device is coated by successively passing portions of the device, without deformation, through the mixtures so that the successive portions are exposed to the mixture for substantially the same time. The tissue exposed portion is formed by thermal methods such as thermal extrusion or molding a mixture of the active agent and the reservoir polymer and/or extrusion or molding of a mixture of the elutable component and the surface layer polymer.

Other objects and features are discussed below.

DESCRIPTION OF THE PREFERRED EMBODIMENT

We first briefly describe the drawings.

Structure

Figure 1:
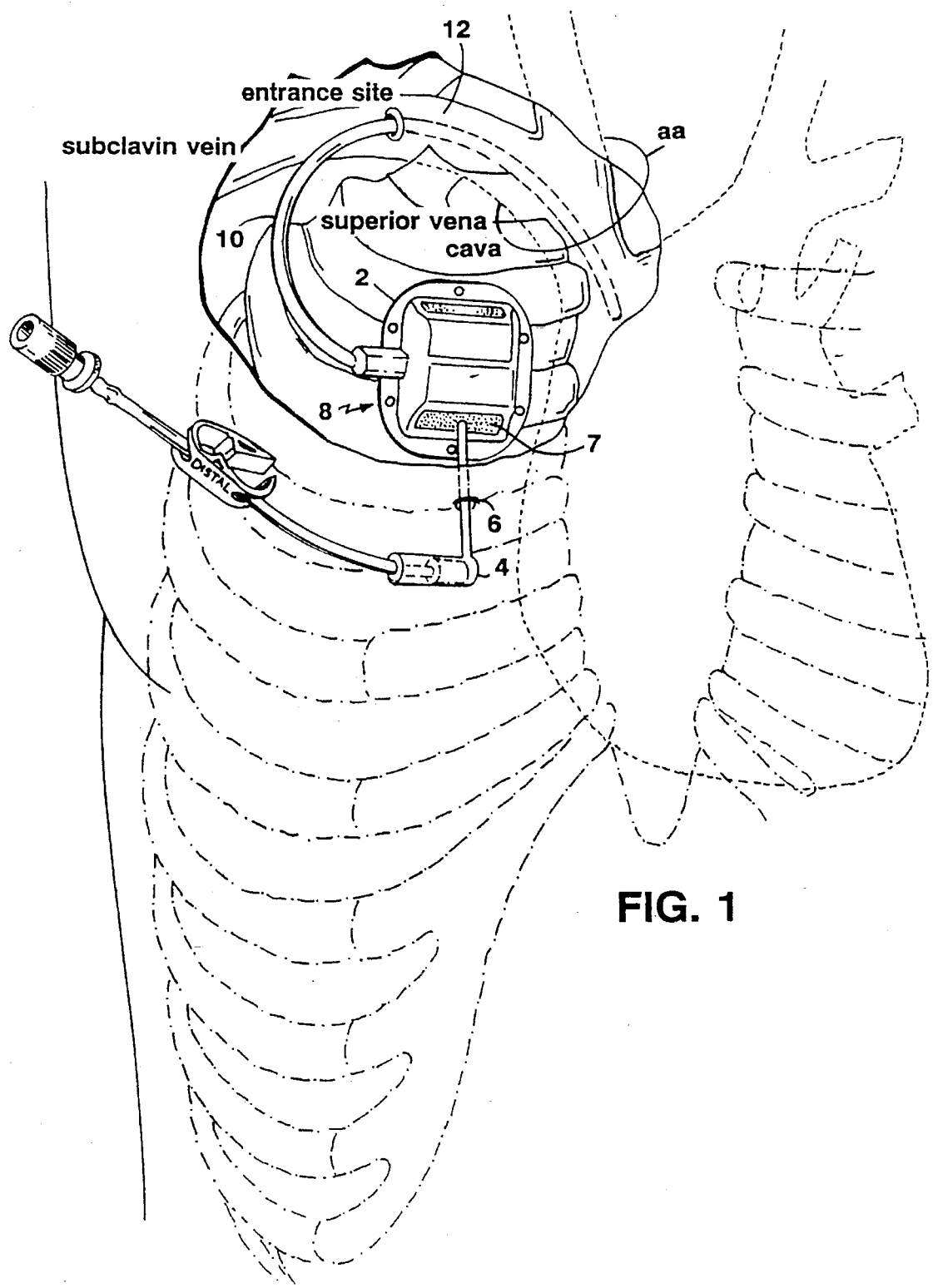
FIG. 1 is a schematic of a drug delivery medical instrument having a polymer coating according to the invention.

Referring to FIG. 1, a subcutaneous drug delivery apparatus 2 is shown (which may be a S.E.A. Porte® implantable vascular access port apparatus, available from Harbor Medical, Boston, Mass.) in which a medicine is introduced to a subcutaneous port 8 in the chest by a needle member 4 which punctures the skin at puncture point or incision 6 in the skin and the port septum 7. A 9-French, 2-lumen polyurethane catheter 10 extends from the port 8 and is introduced to a blood vessel 12 such as the subclavian vein or internal jugular, for delivery of the medicines through one of the lumens 14 (cross-section through one lumen shown in FIG. 1a). The port 8 and catheter 10 typically remain in the patient's body for a period of two weeks or more while the needle is introduced or removed as desired for administering the medicine.

Figure 1A:
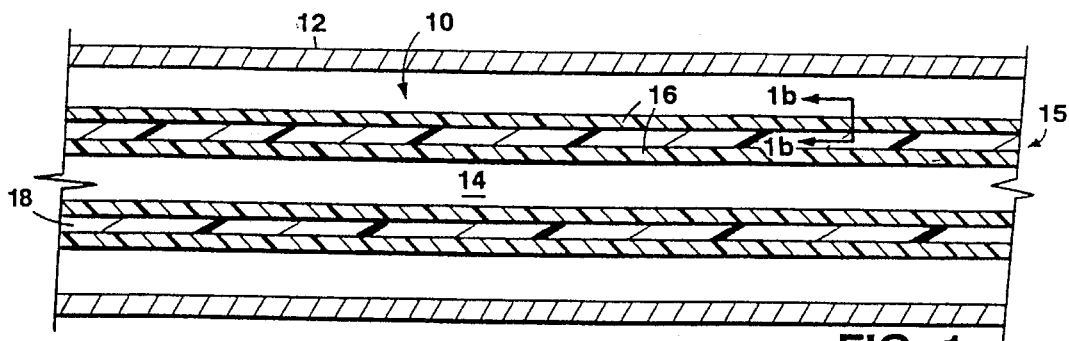
FIG. 1a is an enlarged view of the portion aa of the medical instrument in FIG. 1.

Referring now to the enlarged view of the catheter in the blood vessel in FIG. 1a, the catheter 10 which may occupy nearly the entire blood vessel lumen diameter, includes a thin, polymer release coating 16 exposed to the tissue, i.e., in this example, blood, that enables gradual release of a physiologically active agent, e.g., heparin to inhibit adverse physiological reaction to the device such as thrombus formation during catheterization. Similarly, the walls 15 of the catheter lumen 14 may also include the release coating 16.

Figure 1B:
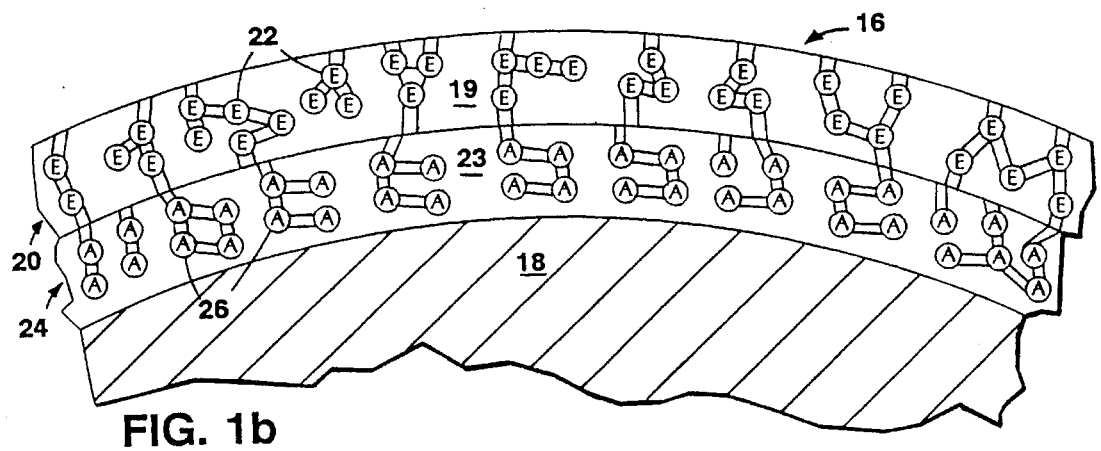
FIG. 1b is a cross-section taken along the line bb in FIG. 1a, greatly enlarged and depicting the polymer prior to substantial exposure to body fluids.

The further enlarged cross-sectional view in FIG. 1b depicts the polymer 16 prior to substantial exposure to body fluids such as blood and plasma. The blood-exposed polymer 16 is a coating, e.g., about 4-mils thick, on the catheter substrate material 18 and includes a polymeric surface-layer 20 (about 2 mils thick) which typically, prior to exposure to body fluids, incorporates elutable components 22, such as communicating pockets of PEO, that are soluble in body fluids and held in a polymer binder 19 such as polyurethane. A reservoir portion 24 (about 2 mils thick) is bonded (for example, mechanically or chemically) directly to the medical instrument substrate 18 and supports (by mechanical or chemical bonding) the outer layer 20. The reservoir incorporates communicating pockets of the physiologically active agent 26 in a polymer binder 23 which may also be polyurethane.

Figure 1C:
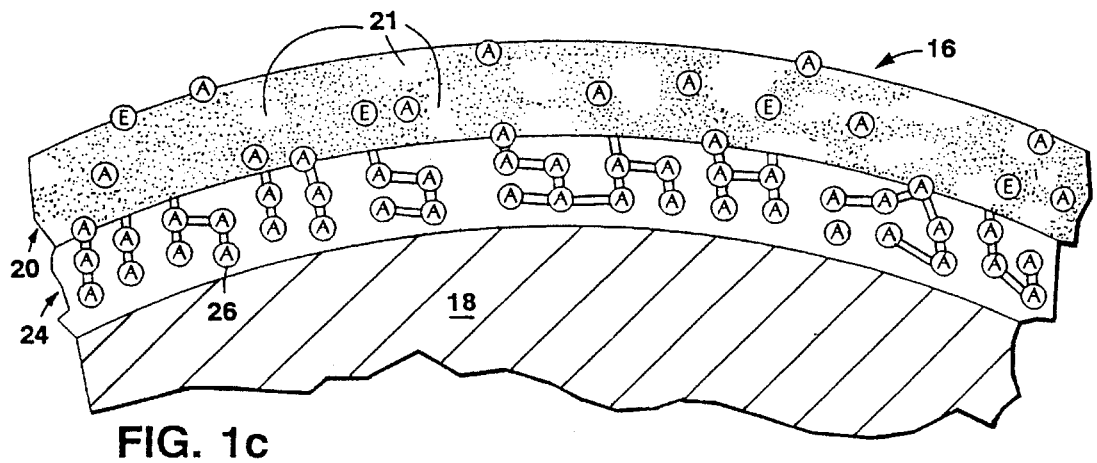
FIG. 1c is the cross-section as shown in FIG. 1b, after exposure of the polymer to body fluids.

Referring now to FIG. 1c, when the polymer 16 is exposed to body fluids, the elutable component 22 goes into solution and is removed from the surface-layer 20 forming a porous network 21 of communicating tortuous passageways through which body fluids may migrate, reach the reservoir portion 24 and enable release of the physiologically active agent 26. The released physiologically active agent diffuses through the body fluid in the pores to the surface of the surface-layer where it interacts with the body fluid in the body lumen to inhibit adverse reactions to the presence of the device. As the agent is released over time, pore structure is formed from the communicating pockets in the reservoir portion, forming a porous network in the reservoir so that agent contained in portions of the reservoir away from the surface-layer may also be released.

Figure 2:
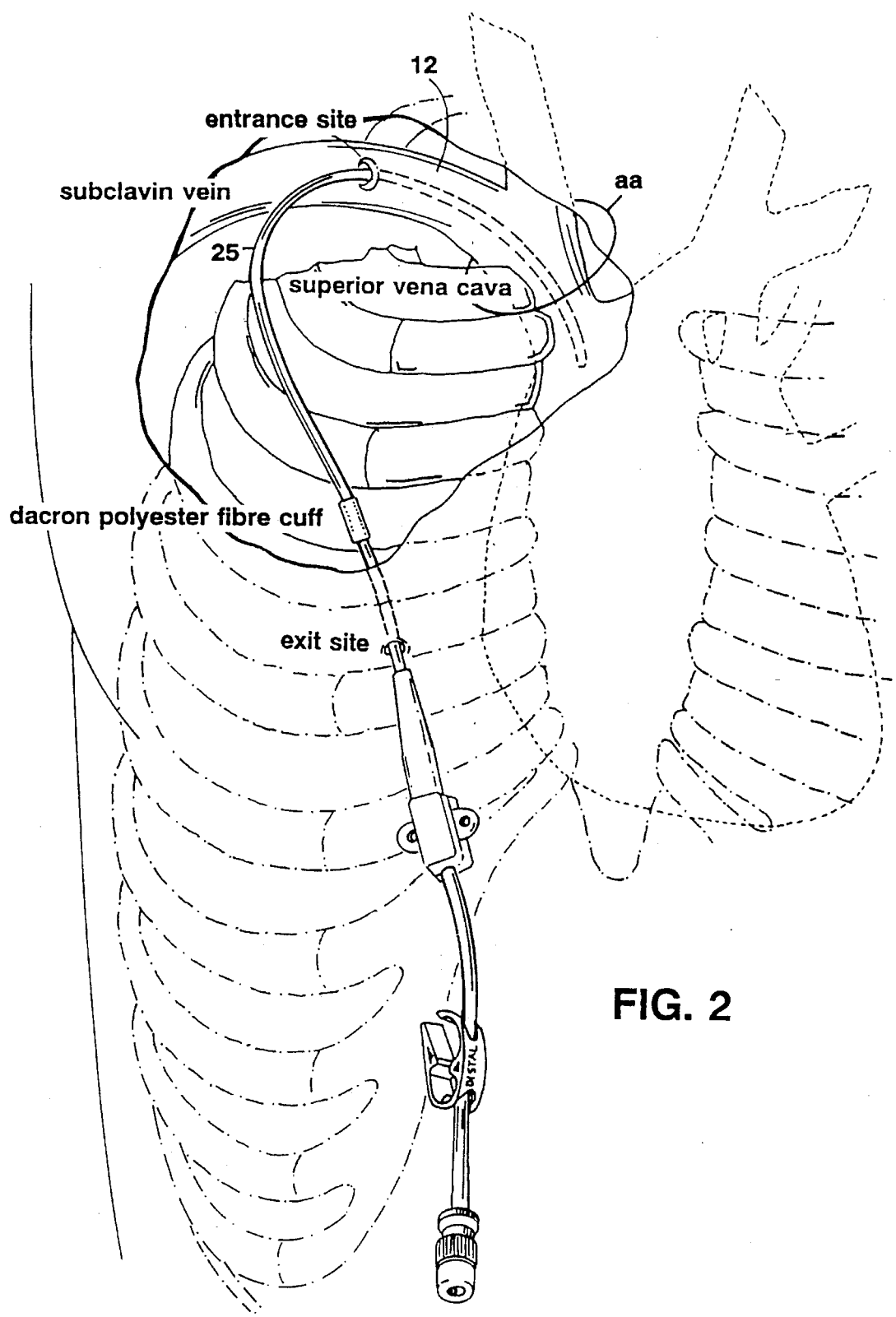
FIG. 2 is a schematic of an alternative drug delivery medical instrument formed of a polymer according to the invention.
Figure 2A:
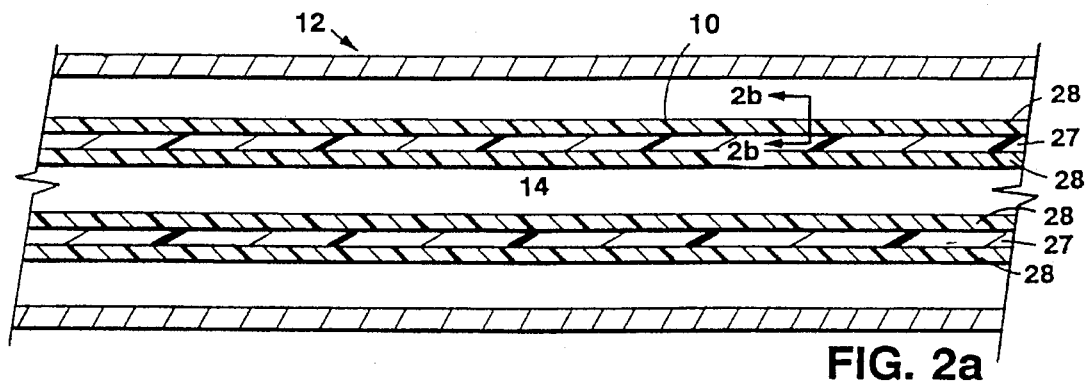
FIG. 2a is an enlarged view of the portion aa of the medical instrument in FIG. 2.
Figure 2B:
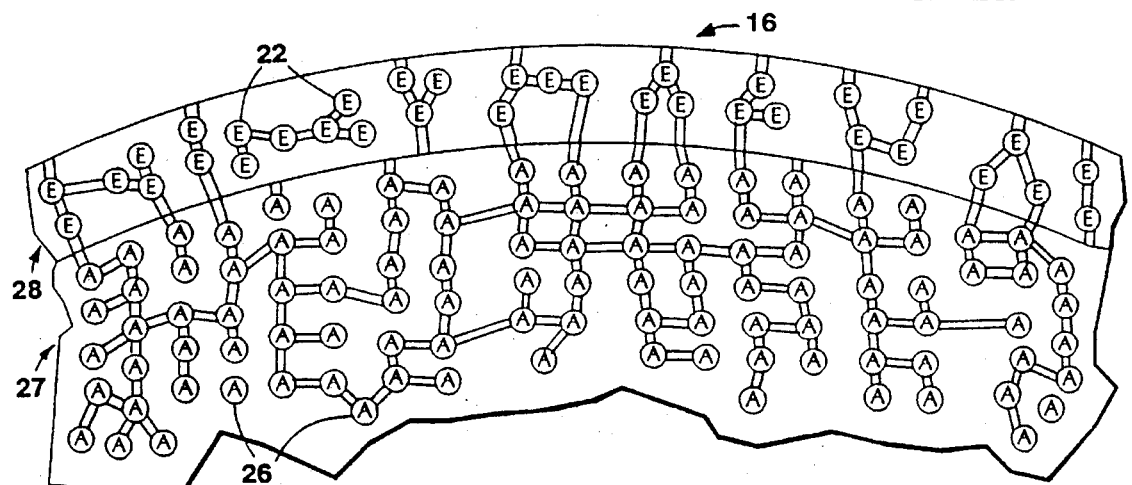
FIG. 2b is a cross-section taken along the lines bb in FIG. 2a, greatly enlarged and depicting the polymer prior to substantial exposure to body fluids.
Figure 2C:
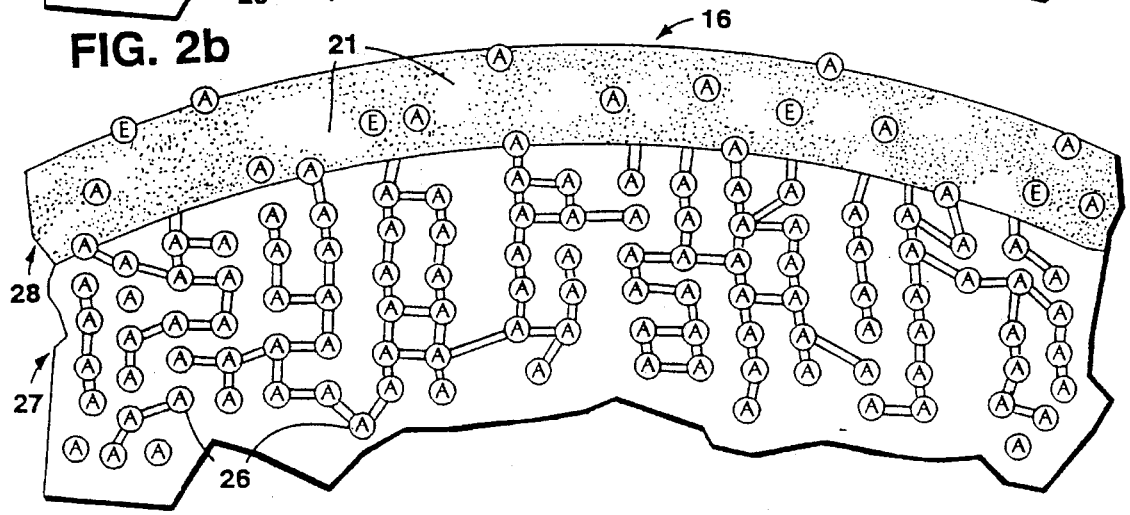
FIG. 2c is the cross-section as shown in FIG. 2b, after exposure of the polymer to body fluids.

Referring now to FIGS. 2–2c, a drug delivery catheter is shown. The catheter 25 which may be, for example, drug delivery catheter is introduced to the patient's body to a blood vessel 12. Referring to FIGS. 2a and 2b, the catheter 25 is formed entirely from a polymer according to the invention. The polymer has a surface-layer 28 exposed to the body lumen and on the walls of the inner catheter lumen 14, that includes elutable material 22. A physiologically active agent is incorporated in the reservoir portion 27 which forms, substantially, the structure of the catheter. As shown in FIG. 2c, after exposure to body fluids, the elutable material of the surface-layer dissolves forming a pore structure 21 through which the physiologically active material may migrate from the reservoir portion.

A catheter as shown in FIG. 2 et seq., formed entirely from a polymer may be used in the subcutaneous drug delivery system as shown in FIG. 1 et seq. and a coated catheter as in FIG. 1 et seq. used in conventional catheter systems, as in FIG. 2 et seq. Further, other parts of the medical instrument may be coated or formed of a release polymer incorporating a beneficial agent. For example, the port 8 in FIG. 1 may include a time release polymer carrying an antiproliferative to inhibit wound response. In addition, different parts of the same instrument may include coatings incorporating different agents. For example in FIG. 2, the portion of the catheter in contact with the tissue adjacent to the incision may include an antiproliferative to inhibit wound response while those portions of the catheter normally positioned within a blood vessel during use may include an anticoagulant such as heparin to inhibit clotting.

The medical devices of the invention having release polymers of the invention enable a gradual, long-time release, on the order of several weeks if desired, of physiologically active agents such as heparin to inhibit adverse reactions to the presence of the medical device. The reservoir portion is formulated to enable substantially free release of the physiologically active agent upon contact with body fluids. In general, the particle size and concentration of active agent are selected to form a communicating network of pockets in the binder of the reservoir. Typically, the particle size is less than about 10 microns, preferably 4 to 8 microns. Particle sizes on the order of the thickness of the reservoir layer may be used, for example, particle sizes of about 50 microns (about 2 mils) for a 2 mil thick reservoir. In some embodiments, high concentrations of active agent, e.g., over 30% by weight are incorporated in the polymer binder. High concentrations are enabled without excessive release rates to the body by the metering effect of the surface-layer, disposed over the reservoir. The reservoir may also include a non-physiologically active elutable component to facilitate formation of pore structure and migration of the physiologically active agent, as desired. In general, the reservoir portion contains from about 10 to 90% by weight, preferably 40 to 60% by weight of agent. The agent may be any body-fluid soluble active material or may be a material that is solubilized by the incorporation of pockets containing a solubilizing agent (e.g. PEO) with a less soluble active agent. Agents with beneficial therapeutic effect relating to the prevention of body-rejection reactions such as thrombus formation, platelet aggregration, or cell proliferation may be incorporated. A preferred example is heparin. Other examples include aspirin, prostoglandins such as prostacyclin, or thrombolytic agents such as tPA, urokinase, streptokinase, prourokinase or antiproliferative agents such as heparin and steroids such as cortisone. Antiproliferative drugs, such as heparin or steroids, may be used, for example, to prevent excessive fibrous tissue formation or contracture that can occur from using devices such as artificial skin or breast prostheses. Additional agents include anti-rejection drugs, such as cyclosporin, to prevent rejection of hybrid artificial organs containing animal cells or tissue; antimicrobial agents such as antibiotics, for example, Vancomycin to prevent infection adjacent to medical devices; peptide or protein drugs such as cell growth factors, for example, epidermal growth factor, platelet derived growth factor or fibroblast growth factor to enhance healthy tissue adjacent to medical devices such as percutaneous connectors; anticalcifying drugs such as diphosphonates to prevent calcification of biomedical materials such as used in heart valves or the artificial heart.

The surface-layer controls or meters the rate of depletion of the active agent that diffuses from the reservoir portion to the surface-layer through the pores. The surface layer preferably is of substantially uniform thickness and covers substantially completely the underlying reservoir so that no portion of the reservoir is directly exposed to the body. The elutable component, incorporated within the surface-layer is an agent that is both biocompatible and soluble in body fluid. The elutable component may also be a slightly soluble material which is incorporated within pockets in the reservoir with a highly soluble solubilizing agent. The elutable component is present in the polymer binder in sufficient concentration and of particle size such that communicating, tortuous channels in the polymer are formed upon exposure to body fluid. The regions or pockets of elutable component are typically from 100 micron to submicron, most preferably less than about 1 micron, in diameter. Larger particles and higher concentrations of elutable component give generally higher rates of active-agent release. In addition, the surface-layer may be configured to maintain the integrity and smoothness of the tissue-exposed portion when the agent has been largely released from the reservoir, leaving a highly porous polymer binder which might otherwise become a site for platelet aggregation. Higher molecular weight elutable components, such as high molecular weight PEO, e.g., molecular weight of about 300,000, may cause a swelling effect in the binder that, while not degrading the performance of the release polymer, may create a visually detectable physical deformation compared to a lower molecular weight, PEO, e.g., molecular weight less than around 100,000. A preferred elutable component is Carbowax® 20M (available from Union Carbide), a PEO with molecular weight of around 20,000.

In general, the elutable component may be colloidal in nature, i.e., it is in the form of particulates of about 1 micron or less, or, the component may be particulate in nature where larger, particles, e.g., larger than 1 micron, preferably less than 10 microns most preferably in the 6 to 8 micron range, are used. The elutable component may also be a biodegradeable component. Particulate elutable agents include, for example, albumin, polyvinylpyrollidone, dextran, elutable components include, for example, polyethylene oxide, polyethylene glycol, polyethylene oxide/polypropylene oxide copolymers, polyhydroxyethyl methacrylate, polyvinylpyrollidone, polyacrylamide and copolymers, soluble celluloses such as hydroxypropyl cellulose and proteins, peptides, polysaccharides and liposomes. The elutable components may also be biodegradeable components such as polylactides, polyanhydrides and polyorthoesters and their copolymers. The elutable component may also be a physiologically active agent or include a physiologically active agent in addition to non-active components to produce a desired gradual release effect. In particular, it is preferred to incorporate a minor amount, for example, about 2% by weight, active agent such as heparin in the surface-layer to provide antithrombogenic effect upon first exposure of the device to blood, while the elutable component dissolves to enable release of the agent from the reservoir (which typically takes 10 to 15 minutes for thin (4 mil) polymer coatings as in FIG. 1).

As shown in FIGS. 1–1c, the polymer may be applied as a coating, which may be a thin, nonswellable coating where the surface-layer and reservoir layer are each about 1 to 100 mils thick, typically 2 to 3 mils (i.e., 0.002 to 0.003 inches) thick, thus enabling entry of the instruments in narrow lumens where the device occupies substantially all of the available lumen diameter. As shown in FIGS. 2–2b, the entire medical instrument also may be formed from the release polymer, enabling a medical instrument without a size-increasing coating. The polymer itself forms the device substrate.

The polymer binder for the surface-layer and reservoir portions may be any material that is compatible with and enables release of the selected physiologically active agent. For coatings on flexible medical instrument substrates, the binder may be selected to have a durometer of equal or more flexibility than that of the substrate to avoid cracking or peeling as the substrate is deformed during use. The binder polymer for the surface-layer and reservoir portions may be the same or different. Pellthane®, 80 AE, medical grade, available from Dow Chemical, Midland, Mich., a ployether urethane including polytetramethyleneglycol as a soft segment, diphenylmethane isocyanate as a hard segment, butanediol chain extender with a durometer of about 80 A is one preferred binder for coatings on drug delivery catheters. Other binder polymers include, for example, polyurethane and its copolymers, silicone and its copolymers, ethylene vinyl acetate, thermoplastic elastomers, polyvinyl chloride, polyolefins, styrene butadiene styrene, cellulosics, polyamides, polytetrafluoroethylenes, polyesters, polycarbonates, polysulfones, acrylics such as polymethyl methacrylate, and acrylonitrile butadiene styrene copolymers. Also suitable are thermoset or curable polymers such as two-part and three-part polymer systems, for example, two-part urethanes, silicones and epoxies.

As coatings, the time release polymer of the invention may be formed on virtually any substrate, for example, polyurethane and its copolymers, silicone and its copolymers, ethylene vinyl acetate, thermoplastic elastomers, polyvinyl chloride, polyolefins, cellulosics, polyamides, polytetrafluoroethylenes, polyesters, polycarbonates, polysulfones, and acrylonitrile butadiene styrene copolymers, acrylics, metals or alloys based on titanium, stainless steel, nickel-chrome, Nitinol or cobalt-chrome; and ceramics of alumina and glass-ceramics such as Macor®.

Manufacture

A particular advantage of the time-release polymers of the invention is the manufacture of coated articles, i.e., medical instruments.

Figure 3:
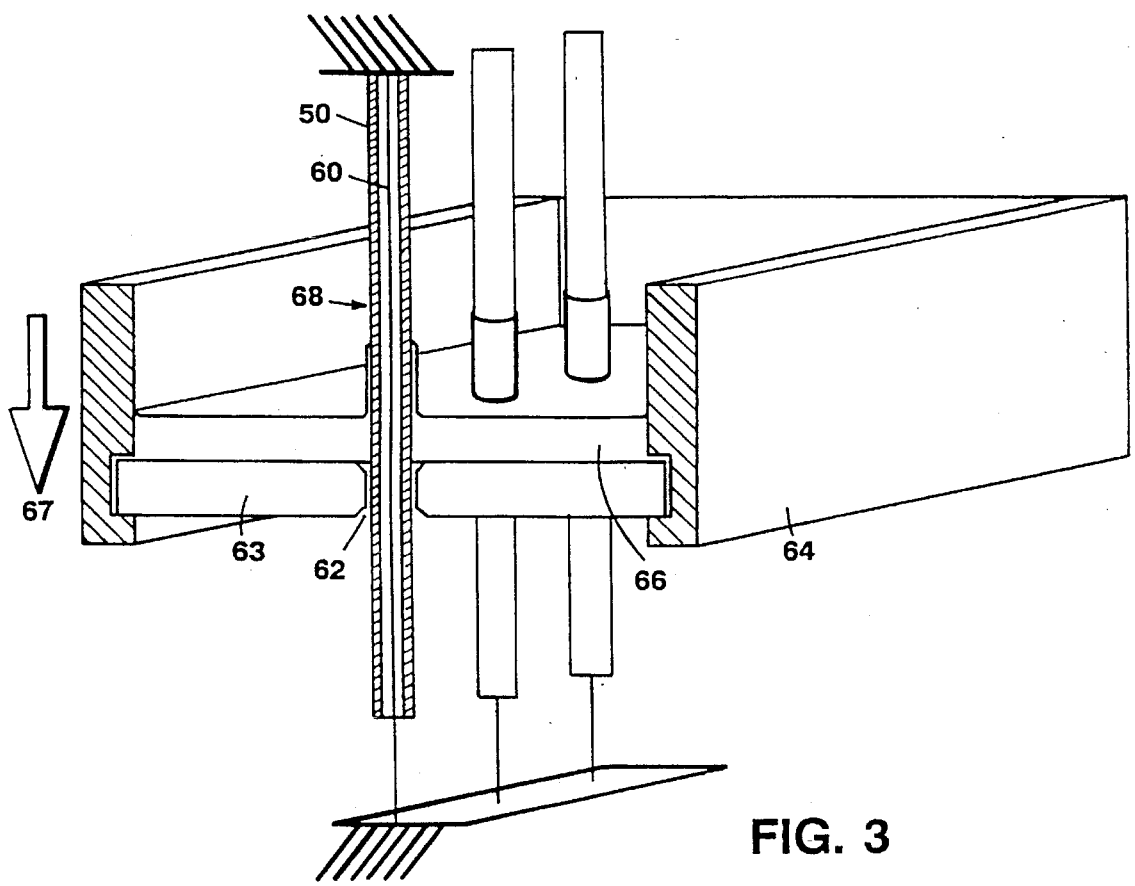
FIG. 3 is a schematic of a coating apparatus for coating medical instruments with a polymer.

Referring now to FIG. 3, the article to be coated such as a catheter 50 may be mounted on a mandrel or wire 60 and aligned with the preformed apertures 62 (slightly larger than the catheter diameter) in the teflon bottom piece 63 of a boat 64 that includes a mixture 66 of polymer at ambient temperature, e.g., 25° C. To form the reservoir portion, the mixture may include, for example, nine Darts solvent, e.g. tetrahydrofuran (THF), and one part Pellthane® polyurethane polymer which includes the desired proportion of ground sodium heparin particles. The boat may be moved in a downward fashion as indicated by arrow 67 to produce a coating 68 on the exterior of catheter 50. After a short (e.g., 15 minutes) drying period, additional coats may be added as desired. After coating, the catheter 50 is allowed to air dry at ambient temperature for about two hours to allow complete solvent evaporation and/or polymerization to form the reservoir portion.

For formation of the surface-layer the boat 64 is cleaned of the reservoir portion mixture and filled with a mixture including a solvent, e.g. THF (9 parts) and Pellthane® (1 part) having the desired amount of elutable component. The boat is moved over the catheter and dried, as discussed above to form the surface-layer. Subsequent coats may also be formed.

An advantage of the dipping method and apparatus described with regard to FIG. 3 is that highly uniform coating thickness may be achieved since each portion of the substrate is successively in contact with the mixture for the same period of time and further, no deformation of the substrate occurs. Generally, for faster rates of movement of the boat 64, thicker layers are formed since the polymer gels along the catheter surfaces upon evaporation of the solvent, rather than collects in the boat as happens with slower boat motion. For thin layers, e.g., on the order of a few mils, using a fairly volatile solvent such as THF, the dipping speed is generally between 26 to 28 cm/min for the reservoir portion and around 21 cm/min for the outer layer for catheters in the range of 7 to 10 F. The thickness of the coatings may be calculated by subtracting the weight of the coated catheter from the weight of the uncoated catheter, dividing by the calcuated surface area of the uncoated substrate and dividing by the known density of the coating. The solvent may be any solvent that solubilizes the polymer and preferably is a more volatile solvent that evaporates rapidly at ambient temperature or with mild heating. The solvent evaporation rate and boat speed are selected to avoid substantial solubilizing of the catheter substrate or degradation of a prior applied coating so that boundaries between layers are formed.

Articles might also be formed entirely from the release polymer. In this case, a prepolymer mixture including the desired quantity of heparin is prepared, formed into the desired shape and polymerized. A prepolymer solution containing an elutable component is next applied over the article and polymerized to form the surface-layer. Additionally, articles may be formed by thermal means such as injection molding a mixture of polymer and active agent. The outer layer may be formed by molding the polymer and elutable agent mixture around the body of the device by insert molding techniques.

Use

The polymers of the present invention may be used in the formation of or the coating of medical devices which contact body various body tissues and bodily fluids. In the embodiments discussed with respect to FIGS. 1 and 2, catheters formed of the release polymer are discussed. Such catheters typically range in size from smaller than 2 F to 12 F. Other devices include vinyl blood storage bags, blood tubing, intravenous catheters, central venous catheters, intra-aortic balloon pumps, artificial heart components, vascular grafts, bovine carotid arteries, heart valves, cardiovascular sutures, total artificial heart, vascular stents and ventricular assist pumps, extracorporeal devices such as blood oxygenators, blood filters, hemodialysis units, hemoperfusion, plasmapheresis, and hybrid artificial organs of the type containing living cells to replace organ functions such as the pancreas or the liver.

EXAMPLES

The following examples are illustrative.

Example 1

A 9 F polyurethane catheter was coated with a 2 mil thick polyurethane reservoir incorporating 40% by weight heparin using a 9.28 wt % solution of Pellthane® in tetrahydrofuran with 40 wt % USP porcine mucosal heparin on a dry weight basis with Pellthane®. A 2 mil thick polyurethane surface-layer incorporating 15 wt % PEO and a minor amount (2 wt %) of heparin using a 9.28 wt % solution of Pellthane® in tetrahydrofuran containing 15 wt % Carbowax 20M® and 2 wt % heparin on a dry weight basis with Pellthane®. The following procedure was employed:

A base Pellthane® solution was prepared by combining Pellthane® pellets as supplied with THF in a clean glass bottle in proportions of 9.09 g of polymer to 100 ml of solvent (number of ml of solvent ×(0.0909)=number of grams of polymer). The bottle was put on a tumbler such as a paint shaker until the pellets dissolved. A bulk heparin solution was prepared by combining in a glass vessel jet milled heparin (sodium heparin USP ground to less than 10 microns) with the base Pellthane® solution in the required amount (weight of heparin, (grams)=weight of base solution ×(0.0619)) to form a 40 wt% solution on a dry weight basis with Pellthane®. Approximately 100 ball bearings (3/16th O.D., cleaned in THF) were placed in the vessel and the vessel placed on the tumbler and allowed to spin until the heparin is mixed (for example, overnight). The bulk heparin solution is stored on the tumbler when not in use.

A bulk Carbowax® solution was prepared by pouring the base Pellthane® solution into a clean glass bottle and the required amount of Carbowax® flakes (weight of Carbowax® (grams)=weight of base solution ×(0.0168)) to form a solution of about 15 wt % Carbowax® on a dry weight basis with Pellthane®. The mixture was placed in an oven for four hours at 50±10° C. to facilitate the solvation of the Carbowax®, shaken for five minutes in a tumbler and allowed to cool for at least three hours at ambient (20°–25° C.) upon which a suspension of colloidal Carbowax® solution was formed as indicated by the translucent, clouded character of the solution. The solution was shaken for about 5 minutes to break up aggregated particles as indicated by the absence of larger white particles (greater than about 10 microns in size). The colloidal suspension, it is thought, creates submicron regions of elutable component in the surface layer.

Prior to applying the coating to the catheter, the solutions were prepared as follows: The bulk heparin solution was poured into a clean glass container and degassed at 20–23 Hg vacuum until all bubbles were gone. A dipping carbowax solution was prepared from a quantity of the bulk Carbowax® solution by combining the required amount of bulk heparin solution (quantity of bulk heparin solution (grams)= quantity of bulk Carbowax® solution ×(0.035)) with the bulk Carbowax® solution to form a solution of 2 wt% heparin and 15 wt % Carbowax® on a dry weight basis with Pellthane® and the mixture shaken for five minutes in a tumbler. Thereafter, the solution was degassed at 20–23 Hg vacuum until all bubbles are gone.

The degassed bulk heparin solution was placed into the dipping boat as was described above with regard to FIG. 3. The dipping speed was about 26 cm/sec and the catheter dipped as described.

After formation of the reservoir portion, the dipping boat was cleaned and the dipping carbowax® solution placed in the dipping boat. The catheter was dipped at about 21 cm/sec to form the outer layer.

Figure 4:
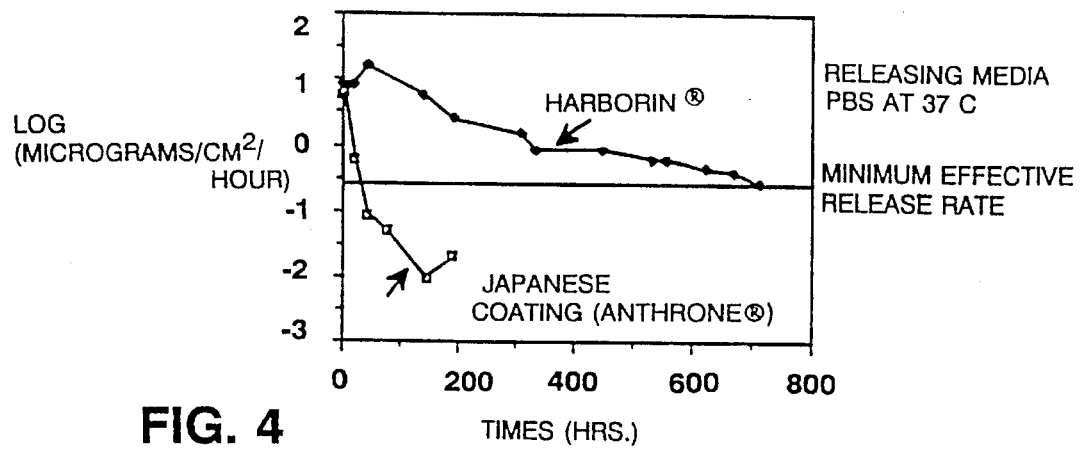
FIG. 4 is a graph comparing heparin release from a polymer having a PEO elutable component according to the invention and a prior art coating.

Table I shows the amount of heparin released for different lengths of the 9 F catheters coated as described above at different time intervals. FIG. 4 shows the release rate of heparin from a catheter coated as discussed above compared to a catheter with a prior art coating, Anthron®, available from Toray Industries, Japan, which is a photoinduced graft polymerization of methoxy poly(ethylene glycol) monomethacrylate and N,N,-dimethylaminoethylmethacrylate on a backbone of a vinyl chloride/vinyl acetate copolymer. (See Hajime Miyama et al., *J. Biomed. Mater. Res.*, Vol. 11, pp. 251–265 (1977).) The Toray polymer is positively charged and binds heparin electrostatically. Release of heparin into phosphate buffered saline was measured using the Azure A assay, under "sink conditions", i.e., the buffer was replaced with fresh buffer solution after each measurement.

In the catheter of the invention, heparin was observed to be released very slowly at the catheter surface creating only a local effect with low systemic dose (based on the calculation of heparin release and body-blood volume). Referring to Table I, during the first day, the total heparin released from a 20 cm length of catheter, 460 units, is equivalent to 6 ml of a standard heparin flush solution of 100 International Units (IU)/ml which is about 1/10 to 1/20 of the typical systemic dose of 5000–10,000 units every 4 to 6 hours). (One IU contains about 6 µg of sodium heparin). The medical instruments of the invention provide local antithrombogenic effects without affecting the blood systemically.

A 1 cm length of a 9 F catheter has a surface area of approximately 1 cm². Therefore, the critical release rate for a 20 cm length of a 9 F catheter would be 0.8 Units/hour (as discussed in Miyama et al., Supra and Lin et al., *Trans. Am. Soc. Artif. Intern. Organs*, Vol. XXXII: 602, (1987)). This critical release rate value is shown by the solid line across FIG. 4 and is equivalent to the 0.24 µg/cm²/hr given in the figure. The catheter coated with the release polymer of the invention, released heparin above this rate for up to one month, in excess of the Anthron® coated catheter which fell below the effective rate after about 50 hours.

TABLE I

Heparin Released for 9 F Catheter-Segment and Time Period

| | Catheter segment length | | | | |
|---|---|---|---|---|---|
| | 1 cm | 5 cm | 10 cm | 15 cm | 20 cm |
| Time Period | | | | | |
| 1 day | 23 IU* | 115 IU | 230 IU | 345 IU | 460 IU |
| 2 to 6 days | 132 | 660 | 1320 | 1980 | 2640 |
| 7 to 14 days | 50 | 250 | 500 | 750 | 1000 |
| 15 to 23 days | 23 | 115 | 230 | 345 | 460 |
| 23 to 27 days | 7 | 35 | 70 | 105 | 140 |
| Total Released | 235 | 1175 | 2350 | 3525 | 4700 |

*International Units

Example 2

Using a technique similar to Example 1, a 9 F polyurethane catheter was coated with a 10 wt % solution of Pellthane® in dimethylacetamide with 40 wt % USP porcine muscosal heparin on a dry weight basis with Pellthane®. The dried reservoir portion was about 2 mils thick. A 10 wt % solution of Pellthane® in dimethylacetamide was applied as the outer layer and contained 20 wt% Dextran (less than 40 microns particle size) on a dry weight basis with Pellthane®. The surface-layer was about 2 mils thick. The release of heparin into phosphate buffered saline was measured using the Azure A assay under sink condition.

Figure 5:
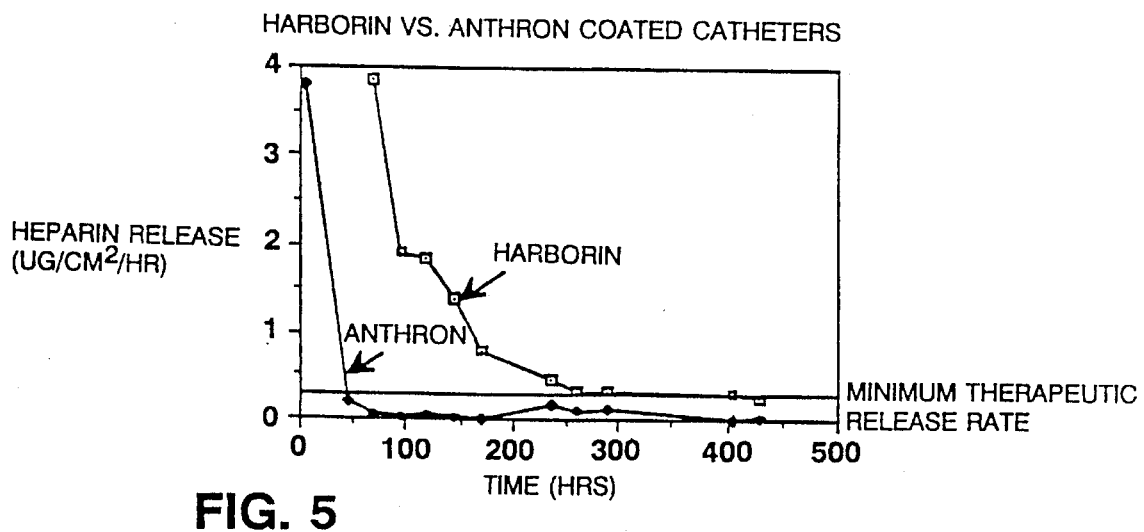
FIG. 5 is a graph comparing the release rate of heparin from a polymer having a dextran elutable component according to the invention and a prior art coating.

As shown in FIG. 5 the catheter of the invention provides an effective release for over 400 hours. By comparison, the heparin release of the prior art Anthron® coating fell below the minimum release rate after about 50 hours.

Example 3

Using a technique similar to Example 1, a 9 F polyurethane catheter was coated with a 10 wt % solution of Pellthane® in dimethylacetamide with 40 wt % USP porcine mucosal heparin on a dry weight basis with Pellthane®. The dried coat was about 2 mils thick. A 10 wt % solution of Pellthane® in dimethylacetamide was applied as the surface-layer and contained 20 wt % human albumin (less than 40 micron particle size) on a dry weight basis with Pellthane®. The surface-layer was about 2 mils thick. Release of heparin into phosphate buffered saline was measured using the Factor Xa assay and the Azure assay. The Factor Xa measures enzymatically active heparin in International Units (IU) while the Azure A measures heparin based on weight (µg) using a colormetric reaction.

Table 2 compares the results of the two assays and compares the release of the catheter of the invention to a catheter coated with Anthron® coating under sink conditions. (IU's were converted to µg using the approximate conversion factor of 6 µg of heparin for each IU). The measurement of enzymatically active heparin released from the samples having the release polymer of the invention as measured by the Factor Xa assay is similar to that demonstrated by the Azure A assay. The minimum effective release rate, as discussed, is 0.24 µg/cm²/hr. The albumin based surface-layer demonstrated effective release for over 200 hours while the Anthron® demonstrate an effective release for less than 48 hours. The data demonstrates that bioactive heparin is being released and that the coating process of the invention does not impair bioactivity.

TABLE 2

| Time | Release Rate-Factor Xa µg/cm²/hr | Release Rate-Azure A µg/cm²/hr |
|---|---|---|
| | Albumin based coating of the invention | |
| 0.5 Hours | 50 | 410 |
| 4 | 202 | 300 |
| 24 | 46 | 22 |
| 48 | 2 | — |
| 100 | 1 | 1 |
| 200 | — | 0.3 |
| | Toray's Anthron ® coating | |
| 0.5 Hours | 26 | 21 |
| 4 | 10 | 9 |
| 24 | 1.4 | 1 |
| 48 | 0.4 | 0.2 |
| 100 | 0 | 0 |
| 200 | 0 | 0 |

Table 3 illustrates the calculated levels of heparin available in the polymer coating of the instant invention of Example 3 based on a 2 mil thick reservoir of 40 wt % heparin compared to the Anthron® coating, based on the manufacturer's data. As the table clearly indicates, the coatings of the invention provide more heparin.

TABLE 3

| Coating Type | Available Heparin* |
|---|---|
| Coating of the invention | 2.5 |
| Anthron ® | 0.35 |

*milligrams per square centimeter

Other embodiments are within the claims.

What is claimed is:

1. A method for forming a medical device the function of which requires exposure to the tissue of a patient, comprising:

forming an internal polymer layer defining a reservoir for a therapeutic agent selected from the group consisting of antithrombogenic agents, antiplatelet agents, prostaglandins, thrombolytic drugs, antiproliferative drugs, antirejection drugs, antimicrobial drugs, growth factors, and anticalcifying agents, that inhibits adverse reaction to the presence of the device, the internal polymer layer comprising a polymer selected from the group consisting of polyurethanes and its copolymers, silicone and its copolymers, ethylene vinylacetate, thermoplastic elastomers, polyvinylchloride, polyolefins, cellulosics, polyamides, polytetrafluoroethylenes, polyesters, polycarbonates, polysulfones, acrylics, and acrylonitrile butadiene styrene copolymers, and, forming a tissue-exposed overlying outer polymer metering layer supported by said internal polymer layer, said outer polymer metering layer having a stable, uniform, predetermined thickness covering the underlying reservoir so that no portion of the reservoir is directly exposed to body fluids, and incorporating a distribution of an elutable component which, upon exposure to body fluids, elutes from said outer polymer metering layer to form a predetermined porous network capable of exposing said therapeutic agent in said reservoir in said internal polymer layer to said body fluid, said elutable component being selected from the group consisting of polyethylene oxide, polyethylene glycol, polyethylene oxide/polypropylene oxide copolymers, polyhydroxyethylmethacrylate, polyvinylpyrollidone, polyacrylamide and its copolymers, liposomes, albumin, dextran, proteins, peptides, polysaccharides, polylactides, polygalactides, polyanhydrides, polyorthoesters and their copolymers, and soluble cellulosics, wherein said reservoir defined by said internal polymer layer incorporates said therapeutic agent in a manner that permits substantially free outward release of said agent from said reservoir into said porous network of said outer polymer metering layer as said elutable component elates from said polymer metering layer, said predetermined thickness of said outer polymer layer and the concentration and particle size of said elutable component are selected to enable said outer polymer metering layer to meter the rate of outward migration of the therapeutic agent from the reservoir through the outer polymer metering layer, and said outer polymer metering layer and said internal polymer layer, in combination, enable prolonged controlled release, at said predetermined dosage level, from said exposed surface of said medical device to the tissue of said patient to inhibit adverse reaction of the patient to the prolonged presence of the body of said medical device in said patient.

2. The method of claim 1 wherein said forming said reservoir portion further comprises:

forming a mixture including a reservoir polymer and said elutable component, forming said reservoir from said mixture;

forming a mixture including a surface-layer polymer and said agent; and forming said surface layer by applying said surface-layer mixture to said reservoir.

3. The method of claim 2 wherein said forming said reservoir mixture further comprises:

mixing said reservoir polymer and said elutable component in a solvent;

and said forming said reservoir further comprises evaporating said solvent to form said reservoir.

4. The method of claim 3 wherein said mixing further comprises:

suspending a particulate elutable component in said solvent.

5. The method of claim 3 wherein said mixing further comprises:

forming a colloidal suspension in said solvent.

6. The method of claim 5 further comprises:

selecting said elutable component from the group consisting of polyethylene oxide, polyethylene glycol, polyethylene oxide/polypropylene oxide copolymers, polyhydroxyethyl methacrylate, polyvinylpyrollidone, polyacrylamide and copolymers thereof cellulosics and liposomes.

7. The method of any one of claims 4 or 5 further comprising:

selecting the size and concentration of said elutable component to produce a continuous network in said polymer.

8. The method of claim 2 or 3 wherein forming said surface layer mixture further comprises:

mixing said reservoir polymer and said agent in a solvent; and forming said surface layer further comprises, evaporating said solvent to form said reservoir.

9. The method of claim 8 further comprising:

selecting the size and concentration of said agent to produce a continuous network in said polymer.

10. The method of claim 1 further comprising:

applying said tissue-exposed portion as a coating to the surface of a medical device substrate.

11. The method of claim 10 further comprising:

forming said tissue exposed portion at least as flexible as said substrate.

12. The method of claim 10 further comprising:

applying said coating by successively passing portions of said device, without substantial deformation, through said mixtures so that said successive portions are exposed to said mixtures for substantially the same time.

13. The method of claim 1 wherein said forming said polymeric reservoir and surface layer comprises forming by thermal extrusion.

* * * * *